US010352989B2

(12) United States Patent
Rajaduray

(10) Patent No.: US 10,352,989 B2
(45) Date of Patent: *Jul. 16, 2019

(54) SYSTEM AND METHOD OF SEMICONDUCTOR CHARACTERIZATION

(71) Applicant: Ramesh Rajaduray, North York (CA)

(72) Inventor: Ramesh Rajaduray, North York (CA)

(73) Assignee: Raja Technologies Inc., Toronto (CA)

( * ) Notice: Subject to any disclaimer, the term of this patent is extended or adjusted under 35 U.S.C. 154(b) by 525 days.

This patent is subject to a terminal disclaimer.

(21) Appl. No.: 14/658,147

(22) Filed: Mar. 14, 2015

(65) Prior Publication Data

US 2016/0003891 A1    Jan. 7, 2016

Related U.S. Application Data

(63) Continuation-in-part of application No. 14/336,046, filed on Jul. 21, 2014, now Pat. No. 9,002,677.

(Continued)

(51) Int. Cl.
*G01R 31/26* (2014.01)
*G01N 21/63* (2006.01)
(Continued)

(52) U.S. Cl.
CPC ......... *G01R 31/2648* (2013.01); *G01N 21/63* (2013.01); *G01N 33/00* (2013.01);
(Continued)

(58) Field of Classification Search
None
See application file for complete search history.

(56) References Cited

U.S. PATENT DOCUMENTS 4,273,421 A * 6/1981 Gurtler ............. G01R 31/2656
356/432
4,286,215 A * 8/1981 Miller ............... G01R 31/2656
324/754.21

(Continued)

OTHER PUBLICATIONS

Mattis, R., Baroody, J., NBS Technical Note 736—Carrier Lifetime Measurement by the Photoconductive Decay Method, pp. 1-56 (Year: 1972).*

(Continued)

*Primary Examiner* — Alexander Satanovsky
*Assistant Examiner* — Lina M Cordero
(74) *Attorney, Agent, or Firm* — Nixon Peabody LLP

(57) ABSTRACT

A method for characterizing a semiconductor sample, said method comprising: shining light on one or more points in said semiconductor sample; measuring one or more voltage decay curves corresponding to said shining of light on said one or more points in said semiconductor sample; extracting one or more intermediate voltage decay curves corresponding to one or more measured voltage decay curves; obtaining one or more normalized decay curves corresponding to one or more intermediate voltage decay curves, each of the said one or more normalized decay curves corresponding to one or more discrete estimates of survival functions; and analyzing said obtained one or more normalized decay curves, said analyzing comprising obtaining one or more discrete estimates of the probability of recombination corresponding to the one or more normalized decay curves, and computing one or more summary statistics corresponding to each of said obtained one or more discrete estimates.

18 Claims, 11 Drawing Sheets

Related U.S. Application Data

(60) Provisional application No. 62/019,460, filed on Jul. 1, 2014.

(51) Int. Cl.
  *G01N 33/00* (2006.01)
  *H01L 31/08* (2006.01)
  *G01R 31/265* (2006.01)

(52) U.S. Cl.
  CPC .......... *G01R 31/2656* (2013.01); *H01L 31/08* (2013.01); *G01N 2033/0095* (2013.01)

(56) References Cited

U.S. PATENT DOCUMENTS

| | | | |
|---|---|---|---|
| 4,564,807 A | | 1/1986 | Ikezi |
| 4,578,641 A | * | 3/1986 | Tiedje ............... G01R 31/2656 136/290 |
| 4,854,710 A | * | 8/1989 | Opsal ................ G01N 21/171 356/432 |
| 4,949,034 A | * | 8/1990 | Imura ............... G01R 31/308 324/642 |
| 4,952,063 A | * | 8/1990 | Opsal ................ G01N 21/171 356/432 |
| 5,025,145 A | * | 6/1991 | Lagowski .......... G01R 31/2656 250/214 R |
| 5,042,952 A | * | 8/1991 | Opsal ................ G01N 21/171 356/432 |
| 5,081,414 A | * | 1/1992 | Kusama ............ G01R 31/2656 324/642 |
| 5,138,255 A | * | 8/1992 | Kusama ............ G01R 31/2656 324/754.06 |
| 5,177,351 A | * | 1/1993 | Lagowski .......... G01R 31/2656 250/215 |
| 5,453,703 A | * | 9/1995 | Goldfarb ........... G01R 31/2656 324/754.23 |
| 5,667,300 A | * | 9/1997 | Mandelis ........... G01N 25/18 257/E21.53 |
| 5,760,594 A | * | 6/1998 | Lee .................. G01R 31/2648 257/E21.53 |
| 5,929,652 A | * | 7/1999 | Ahrenkiel ......... G01R 31/2656 257/E21.531 |
| 6,275,060 B1 | * | 8/2001 | Ahrenkiel ......... G01R 31/2656 257/E21.531 |
| 7,898,280 B2 | | 3/2011 | Kamieniecki |
| 8,581,613 B2 | * | 11/2013 | Ahrenkiel ......... G01R 31/2648 324/754.23 |
| 9,001,677 B2 | * | 4/2015 | Kim .................. H04W 74/002 370/252 |
| 9,002,677 B1 | * | 4/2015 | Rajaduray ......... G01R 31/2656 702/179 |
| 2002/0011852 A1 | | 1/2002 | Mandelis |
| 2004/0010394 A1 | * | 1/2004 | Koveshnikov ..... G01R 31/2831 702/183 |
| 2004/0224192 A1 | | 11/2004 | Pearson |
| 2008/0061796 A1 | | 3/2008 | Takada |
| 2009/0015579 A1 | | 1/2009 | Nachman |
| 2010/0060307 A1 | | 3/2010 | Kamieniecki |
| 2011/0278702 A1 | | 11/2011 | Horzel |
| 2012/0072648 A1 | | 3/2012 | Shiino |
| 2012/0259562 A1 | | 10/2012 | Booth |
| 2012/0286806 A1 | * | 11/2012 | Machuca .......... G01R 31/2648 324/655 |
| 2012/0307242 A1 | | 12/2012 | Locklin |
| 2013/0169283 A1 | * | 7/2013 | Lagowski .......... G01R 31/305 324/501 |
| 2013/0257472 A1 | | 10/2013 | Kamieniecki |
| 2013/0278576 A1 | | 10/2013 | Lee |
| 2013/0278749 A1 | | 10/2013 | Mandelis |
| 2014/0253161 A1 | * | 9/2014 | Li .................... G01R 1/06783 324/754.04 |
| 2014/0300374 A1 | | 10/2014 | McKenzie |

OTHER PUBLICATIONS

Ramesh Rajaduray, "Investigation of Spatial Characterization Techniques in Semiconductors", Honours Thesis, 1998, Department of Electrical and Electronic Engineering, University of Western Australia.

W. Van Roosbroeck, "Injected Current Carrier Transport in a Semi-Infinite Semiconductor and the Determination of Lifetimes and Surface Recombination Velocities." Journal of Applied Physics 26.4 (1955): 380-391.

J. S. Blakemore, "Semiconductor Statistics", Oxford Pergamon 1962 pp. 330-342.

V. C. Lopes et al "Characterization of (Hg,Cd)Te by the Photoconductive Decay Technique," J. Vac Sci, vol. 8, No. 2, pp. 1167-1170, Mar./Apr. 1990.

R. G. Pratt et al "Minority carrier lifetime in n-type Bridgman grown Hg1-xCdxTe," J. Appl. Physics vol. 54, No. 9 pp. 5152-5157, 1983.

G. Nimtz, et al. "Transient carrier decay and transport properties in Hg1-xCdxTe." Phys. Rev. Bio p. 3302 (1974).

F. Bartoli et al. "Auger-limited carrier lifetimes in HgCdTe at high excess carrier concentrations." Journal of Applied Physics vol. 45 No. 5 pp. 2150-2154 (1974).

D. A. Redfern et al "On the transient photoconductive decay technique for lifetime extraction in HgCdTe" in Optoelectronic and Microelectronic Materials Devices, 1998. Proceedings. 1998 Conference on, pp. 275-278. IEEE, 1999.

Yoo, S. D., & Dal Kwack, K. (1998). Analysis of carrier concentration, lifetime, and electron mobility on p-type HgCdTe. Journal of applied physics, 83(5), 2586-2592.

D. Schoenfeld, "Partial residuals for the proportional hazards regression model." Biometrika vol. 69 No. 1 pp. 239-241 (1982).

E. A. Gehan, "A generalized Wilcoxon test for comparing arbitrarily singly-censored samples." Biometrika vol. 52, No. 1-2 pp. 203-223 (1965).

N. Breslow "A generalized Kruskal-Wallis test for comparing K samples subject to unequal patterns of censorship." Biometrika vol. 57 No. 3 pp. 579-594 (1970).

R. E. Tarone et al "On distribution-free tests for equality of survival distributions." Biometrika vol. 64 No. 1 pp. 156-160 (1977).

A. Renyi "On the Theory of Order Statistics" Acta Mathematica Hungarica vol. 4 pp. 191-231, 1953.

Klein et al "Survival Analysis: Techniques for Censored and Truncated Data" pp. 191-202 and pp. 214-221, Springer, 1997.

S N Singh, R Gandotra, P K Singh and B C Chakravarty (Application of photoconductivity decay and photocurrent generation methods for determination of minority carrier lifetime in silicon, vol. 28, No. 4, Jul. 2005, pp. 317-323.

Balakrishnan, N. et al., "Handbook of Statistics: Advances in Survival Analysis," vol. 23, 2004, Elsevier B.V. (42 pages).

Fleming, T.R. et al., "Counting processes and Survival Analysis," vol. 169, 2011, Wiley, pp. 90-107 (9 pages).

Therneau, T.M. et al, "Modeling Survival Data: Extending the Cox Model," 2000, Springer-Verlag (19 pages).

Tomlin, T., "Spatial Mapping of Minority Carrier Lifetime in Mercury Cadmium Telluride," Honours Thesis, 1995, University of Western Australia, pp. 51-56 (6 pages).

* cited by examiner

SYSTEM AND METHOD OF SEMICONDUCTOR CHARACTERIZATION

CROSS-REFERENCE TO RELATED APPLICATIONS

This application is a continuation-in-part of and claims priority to U.S. patent application Ser. No. 14/336,046 filed on Jul. 21, 2014, now U.S. Pat. No. 9,002,677; and claims the benefit of U.S. Provisional Patent Application No. 62/019,460, filed on Jul. 1, 2014, each of which is incorporated herein by reference in its entirety.

FIELD OF THE INVENTION

The present disclosure relates to characterization of semiconductors.

BRIEF SUMMARY

A method for characterizing a semiconductor sample, said method implemented using an analysis system comprising: a transient photoconductive decay measurement subsystem, a database, a data analysis subsystem, and a statistical analysis subsystem, said transient photoconductive decay measurement subsystem, database, data analysis subsystem and statistical analysis subsystem connected to each other by an interconnection, said method comprising the steps of: shining, using the transient photoconductive decay measurement subsystem, light on one or more points in said semiconductor sample; measuring, using the transient photoconductive decay measurement subsystem, one or more voltage decay curves corresponding to said shining of light on said one or more points in said semiconductor sample; extracting, using the data analysis subsystem, one or more intermediate voltage decay curves corresponding to one or more measured voltage decay curves; obtaining, using the data analysis subsystem, one or more normalized decay curves corresponding to one or more intermediate voltage decay curves, each of the said one or more normalized decay curves corresponding to one or more discrete estimates of survival functions; analyzing, using the statistical analysis subsystem, said obtained one or more normalized decay curves, said analyzing comprising obtaining one or more discrete estimates of the probability of recombination corresponding to the one or more normalized decay curves, and computing one or more summary statistics corresponding to each of said obtained one or more discrete estimates; and determining, by either the statistical analysis subsystem or the data analysis subsystem, the presence of nonuniformities within said semiconductor sample based on results of said analyzing.

A method for characterizing a semiconductor sample, said method comprising: measuring a plurality of voltage decay curves corresponding to a plurality of points in said semiconductor sample; extracting a plurality of intermediate voltage decay curves corresponding to said plurality of measured voltage decay curves; converting said extracted plurality of intermediate voltage decay curves to a plurality of minority carrier population decay curves; performing one or more comparisons of survival behavior using said plurality of minority carrier population decay curves; and determining presence of nonuniformities within said semiconductor sample using said results from said performing of one or more comparisons of survival behavior.

A method for comparing a plurality of semiconductor samples, said method comprising: measuring a plurality of voltage decay curves corresponding to a plurality of points from said plurality of semiconductor samples; extracting a plurality of intermediate voltage decay curves corresponding to said plurality of measured voltage decay curves; converting said extracted plurality of intermediate voltage decay curves to a plurality of minority carrier population decay curves; performing one or more comparisons of survival behavior using said plurality of minority carrier population decay curves; and determining presence of nonuniformities within said plurality of semiconductor samples using said results from said performing of one or more comparisons of survival behavior.

The foregoing and additional aspects and embodiments of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the disclosure will become apparent upon reading the following detailed description and upon reference to the drawings.

Figure 1:
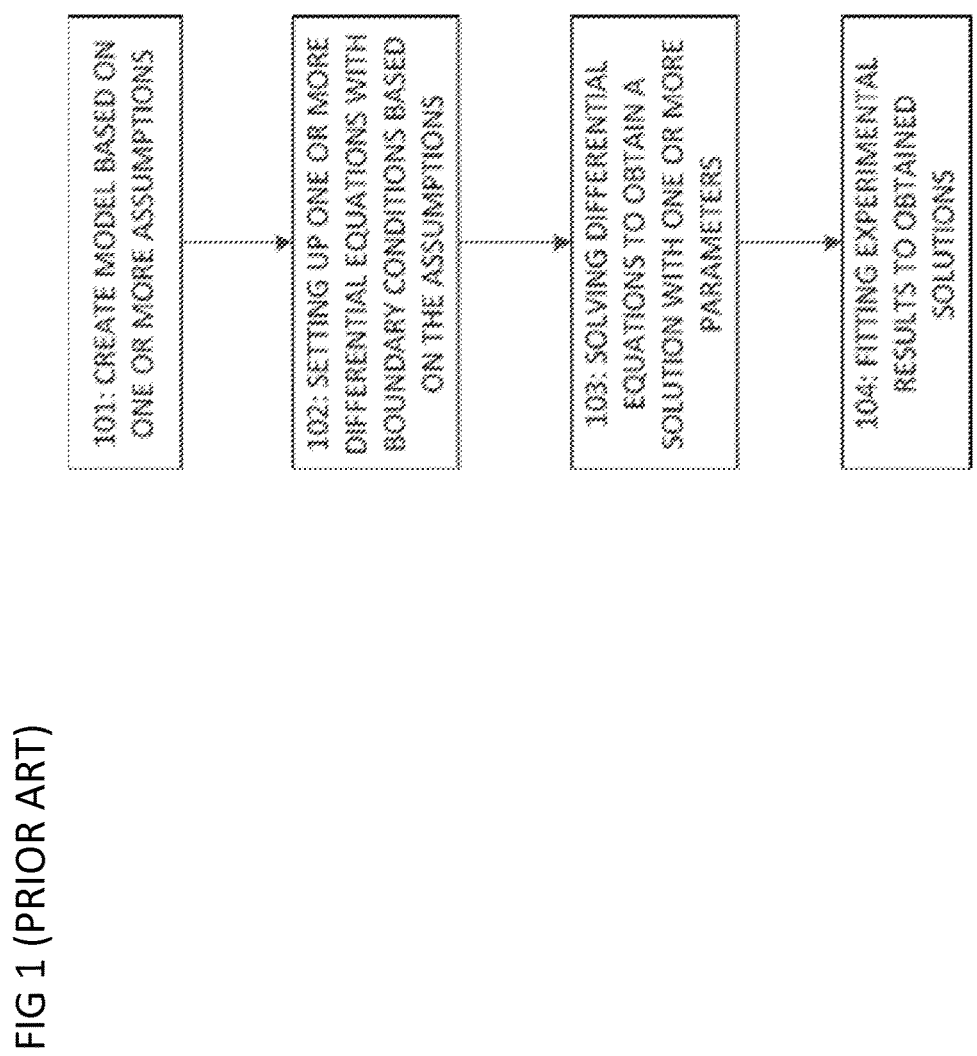
FIG. 1 shows the steps used in the prior art analysis approaches

While the present disclosure is susceptible to various modifications and alternative forms, specific embodiments or implementations have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of an invention as defined by the appended claims.

DETAILED DESCRIPTION

While the description here focuses on analysis of results obtained using the transient photoconductive decay technique, it is equally applicable to the analysis of results obtained using other similar techniques, that is, where a population is generated, and a measurable output related to the survival of the generated population is measured.

Similarly while many of the examples here are discussed in relation to mercury cadmium telluride (HgCdTe), the analyses are equally applicable to any semiconductor material.

Introduction

In the transient photoconductive decay technique, in one embodiment a current is passed through a sample which is to be measured. As a result, a voltage is created across the sample. The voltage is proportional to the resistance of the sample, which in turn is proportional to the resistivity and hence inversely proportional to the conductivity of the sample.

Then, light is shone upon the sample to generate electron hole pairs. Depending on whether the sample is p-type or n-type, either electrons or holes are the minority carriers. As a result, the conductivity of the sample increases, leading to a drop in the resistance of the sample. As a consequence of the resistance drop, the voltage across the sample will also drop.

The generated minority carriers drift under the influence of the bias field created by the voltage and diffuse throughout the sample due to the concentration gradient. Over time, these minority carriers will also recombine within the sample. As a consequence of the recombination of the minority carriers, the conductivity will decay to its value before the light was shone upon the sample. As the conductivity decays so does the resistance, and consequently the voltage across the sample will also increase.

The aim of the transient photoconductive decay technique is to analyse the decay of the induced transient increase in conductivity by measuring the change in voltage across the sample. The sample can be characterized using this technique.

A variation of the transient photoconductive decay technique is spatial mapping. In this variation, light is shone on different locations of the sample, and the resultant transient photoconductive decay curves are measured. By doing so, spatial variations across a sample can be characterized.

Material Parameters

In previous works, several parameters of interest have been characterized using the transient photoconductive decay technique. Some of these parameters are described in section 1.3 of R. Rajaduray, "Investigation of Spatial Characterisation Techniques in Semiconductors," Honours Thesis 1998, University of Western Australia, herein incorporated by reference as if reproduced in its entirety.

Two parameters of interest which have been characterized in previous works are the bulk minority carrier lifetime and the surface recombination velocity.

The bulk minority carrier lifetime $\tau_b$ is the average time a minority carrier identified at a particular instant and location within the bulk of a semiconductor will exist until recombination. It is defined by:

$$\tau_b = \frac{p - p_o}{R}$$

where
p is the total minority carrier density
$p_o$ is the equilibrium minority carrier density
R is the minority carrier recombination rate The bulk minority carrier lifetime $\tau_b$ is highly dependent upon the nature of the recombination mechanisms within the bulk of the semiconductor.

The surface recombination velocity s is a measure of the recombination rate of minority carriers at the surface of a semiconductor. It is defined for excess holes in an n-type semiconductor with a surface at x=0 by:

$$s = D_a \frac{\partial p}{\partial x} \frac{1}{p} \bigg|_{x=0}$$

where
$D_a$ is the ambipolar diffusion coefficient
p is the excess hole concentration
For excess electronics in a p-type semiconductor with a surface at x=0:

$$s = D_a \frac{\partial n}{\partial x} \frac{1}{n} \bigg|_{x=0}$$

where
$D_a$ is the ambipolar diffusion coefficient
n is the excess hole concentration Physically, the surface recombination velocity can be understood as follows: A current of holes or electrons of density p or n drift with an average velocity equal to the surface recombination velocity s into the surface and the holes or electrons are then removed. Thus, as the surface recombination velocity increases, the excess hole or electron concentration at the surface decreases.

Recombination Mechanisms

A detailed explanation of examples of various bulk recombination mechanisms in, for example, HgCdTe is given in Sections 2.2.1 to 2.2.3 of R. Rajaduray, "Investigation of Spatial Characterisation Techniques in Semiconductors," Honours Thesis 1998, University of Western Australia.

For example, with reference to HgCdTe three important bulk recombination mechanisms are Auger, radiative and Shockley-Read-Hall (SRH) recombination. Auger and radiative recombination are strongly dependent upon the carrier concentrations and energy gap. SRH recombination is associated with the presence of defect states within the bandgap, known as traps.

There may be other bulk recombination mechanisms present in other semiconductor materials.

Similarly, an explanation of surface recombination mechanisms in HgCdTe is given in section 2.3 of R. Rajaduray, "Investigation of Spatial Characterisation Techniques in Semiconductors," Honours Thesis 1998, University of Western Australia.

Three surface recombination mechanisms in HgCdTe are:
Thermal transitions through Shockley-Read-Hall centres in the depletion region: This process is similar to the SRH bulk recombination mechanism.
Thermal transitions via fast surface states.
Tunnel transitions through the Shockley-Read-Hall centres in the depletion region There may be other surface recombination mechanisms present in other semiconductor materials.

Previous Analysis Approaches

Many of the existing analysis approaches are based on parametric techniques. FIG. 1 shows the steps involved in the prior art analysis approaches:
101: Creating a model based on one or more assumptions
102: Setting up one or more differential equations with boundary conditions based on the assumptions

103: Solving the differential equations to obtain a solution with one or more parameters which shows the expected behavior of the decay of the minority carrier population over time, and

104: Fitting experimental results to the obtained solution using, for example, least squares fitting to extract the one or more solution parameters.

Two examples of steps 101-103 are explained below. The first example uses the approach detailed in W. Van Roosbroeck, "Injected Current Carrier Transport in a Semi-Infinite Semiconductor and the Determination of Lifetimes and Surface Recombination Velocities." Journal of Applied Physics 26.4 (1955): 380-391. The solution is given as:

$$p(U)=p(0)\exp\ [U(S^2-1)]erfc[S\sqrt{U}] \qquad (1)$$

where

U is time t normalized with respect to $\tau_b$ $\tau_b$ is the bulk minority carrier lifetime p(U) is the minority carrier population at normalized time U or at time $t=U\times\tau_b$ p(0) is the minority carrier at normalized time U=0 or equivalently t=0

S is the normalized surface recombination velocity. S is further given by:

$$S = \frac{s\tau_b}{L}$$

where s is the surface recombination velocity

L is the minority carrier diffusion length, given by $\sqrt{(D_a \times \tau_b)}$ The second example of steps 101-103 provides a solution for a finite rectangular sample of dimensions 2A, 2B and 2C and uses the approach detailed in J. S. Blakemore, Semiconductor Statistics, Oxford Pergamon 1962. The solution is given as a series of eigenfunctions for different modes (i,j,k) and is given by:

$$p(t) = \frac{p(0)}{ABC} \sum_{ijk} K_{ijk} \times \exp[-t(v_b + v_{ijk})] \qquad (2)$$

where p(t) is the minority carrier population at time t p(0) is the minority carrier at time t=0

$K_{ijk}$ is the constant for mode (i, j, k)

$v_{ikj}$ is the inverse of the time constant for mode (i, j, k)

$v_b$ is the inverse of the bulk minority carrier lifetime $\tau_b$

Then, once a solution such as in equations (1) and (2) above have been provided, experimentally obtained decay curves can be fitted to these curves using, for example, least squares regression. The parameters used to obtain the best fit are extracted and recorded. For example, using the Van Roosbroeck model, the surface recombination velocity s and bulk minority carrier lifetime $\tau_b$ to obtain the best fit are extracted.

There are other analysis approaches which are variations of these 2 approaches. Usually, these variations employ slightly different assumptions to create a model. However many of these approaches are flawed for several reasons.

Many of the existing approaches use models which employ unrealistic assumptions and then set up differential equations and boundary conditions based on these unrealistic conditions.

For example, firstly many of the models assume that recombination parameters such as the bulk minority carrier lifetime and the surface recombination velocity are spatially and temporally constant within the analyzed semiconductor sample. This has clearly been shown not to be the case. Studies such as those performed by V. C. Lopes et at "Characterization of (Hg, Cd)Te by the Photoconductive Decay Technique," J. Vac Sci, vol. 8, no. 2, pp. 1167-1170, March/April 1990; and R. G. Pratt et at "Minority carrier lifetime in n-type Bridgman grown $Hg_{1-x}Cd_xTe$," J. Appl. Physics vol 54, no. 9 pp. 5152-5157, 1983; showed spatial nonuniformity of bulk lifetime across semiconductor samples. Furthermore, as shown in Chapter 6 of Ramesh Rajaduray, "Investigation of Spatial Characterisation Techniques in Semiconductors," Honours Thesis 1998, University of Western Australia, the extracted parameters clearly exhibited temporal nonuniformity, that is, when segments of a voltage decay curve with differing temporal extents were fitted to equation (1), the values of the extracted parameters were non-uniform.

Secondly, many of the models assume that the dominant recombination mechanism is independent of the minority carrier density. This is also unrealistic, when it has been shown in that in certain situations, minority carrier concentration dependent recombination mechanisms such as Auger recombination will dominate in materials such as HgCdTe. As an example, in pages 53 and 54 of Ramesh Rajaduray, "Investigation of Spatial Characterisation Techniques in Semiconductors," Honours Thesis 1998, University of Western Australia, it was shown that at time t=0, a population of minority carriers equivalent to 19% of the total number of minority carriers is generated within a small area. It was shown in, for example, G. Nimtz, et al. "Transient carrier decay and transport properties in $Hg_{1-x}Cd_xTe$." Phys. Rev. BIO p 3302 (1974); and F. Bartoli et al. "Auger-limited carrier lifetimes in HgCdTe at high excess carrier concentrations." Journal of Applied Physics vol. 45 no. 5 pp. 2150-2154 (1974); that under such conditions Auger recombination is likely to dominate over radiative and Shockley-Read-Hall mechanisms.

Furthermore, as was pointed out by D. A. Redfern et al "On the transient photoconductive decay technique for lifetime extraction in HgCdTe" in Optoelectronic and Microelectronic Materials Devices, 1998. Proceedings. 1998 Conference on, pp. 275-278. IEEE, 1999, "none of the current models unambiguously [explained] experimental results and that detailed lifetime extraction by photoconductive decay is still not a quantitative technique."

In addition, the generation and recombination of minority carriers which occur within a semiconductor sample each time light is incident on the sample, are random processes. As a consequence, carrier concentrations at particular points within a semiconductor sample are also likely to vary randomly as well. This means that diffusion based movements, which are highly dependent on concentration gradients, are also likely to be random in nature. As a consequence, this further intensifies the random behavior of the carrier concentration at a particular point within a semiconductor sample. If carrier concentration dependent recombination mechanisms dominate, then the random behavior is even further intensified. However many of the differential equations set up in steps 101-104 of FIG. 1 above are assumed to be deterministic in nature.

As a consequence of the above, many of the previously proposed models employ unrealistic assumptions which lead to an incorrect understanding of the evolution of the population of generated minority carriers over time within a semiconductor sample.

As a further consequence, analysis approaches which use such models to perform spatial mapping of recombination parameters, such as, for example, spatial bulk minority carrier lifetime mapping are inherently flawed. Not only is the understanding of the evolution of the population over time wrong, but the incorrect behavior is then used to detect parameter variations which is fundamentally opposite to the assumptions employed.

Therefore there is a need for analysis approaches which are less reliant on using models with inherently unrealistic assumptions to perform parametric-based analysis, or worse still: Using models built on certain assumptions with the aim of detecting properties which are in direct opposition to these assumptions.

New Analysis Approaches

This section demonstrates several analysis approaches which overcome the problems due to the parametric analysis approaches used previously.

Figure 2:
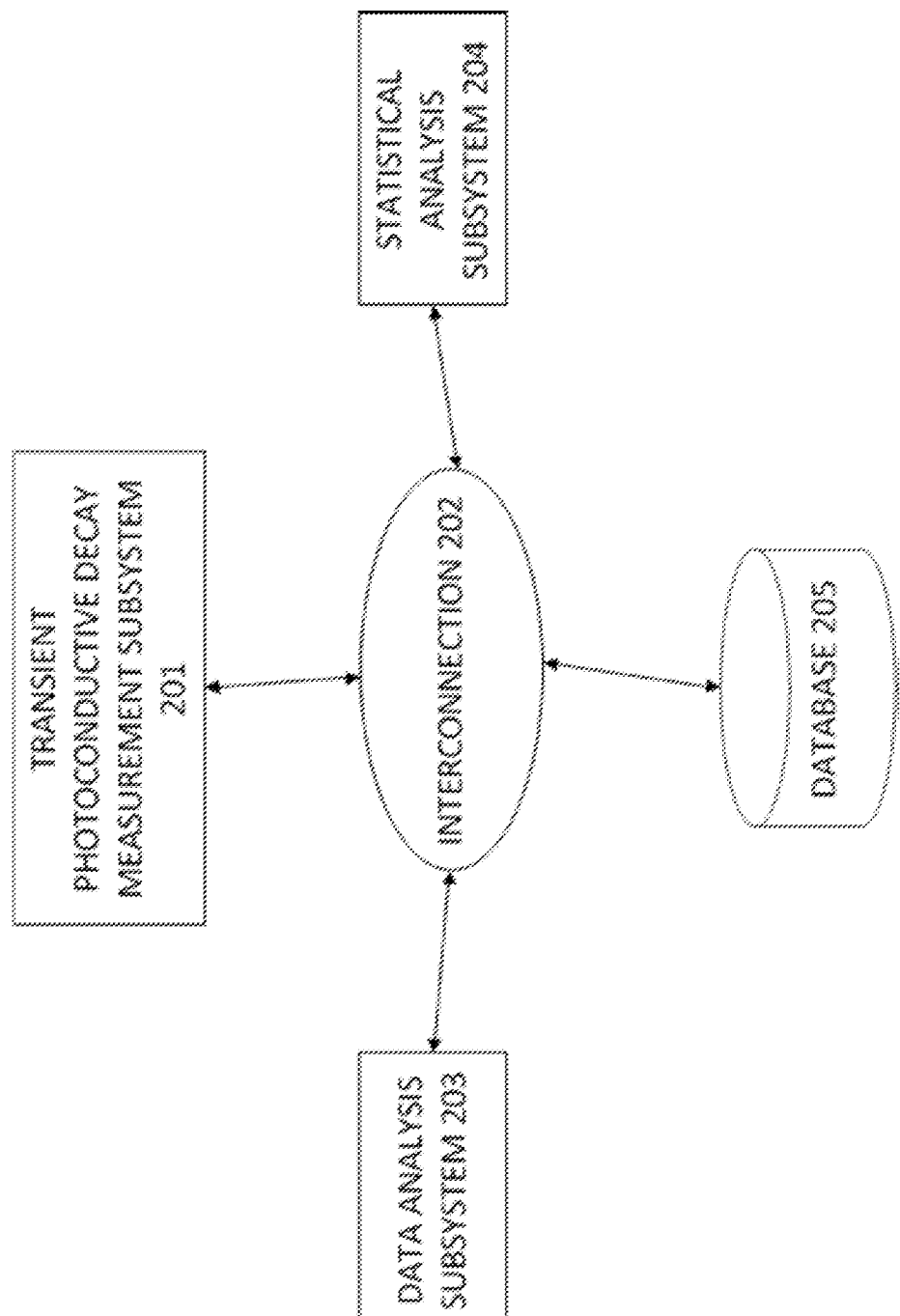
FIG. 2 shows an example analysis setup.
Figure 3:
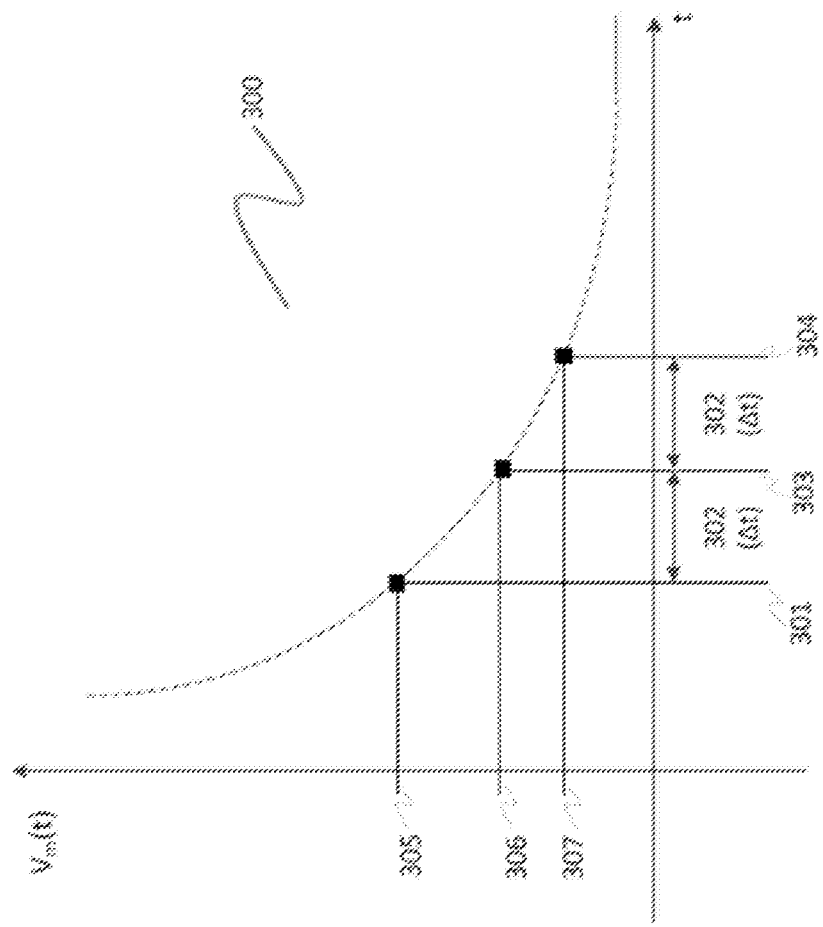
FIG. 3 shows a sample voltage decay curve 300.

An example analysis setup is shown in FIG. 2. Transient photoconductive decay measurement subsystem 201 is used to obtain voltage decay curves for a semiconductor sample. In one embodiment, transient photoconductive decay measurement subsystem 201 is similar to that detailed in section 5.3 of Ramesh Rajaduray, "Investigation of Spatial Characterisation Techniques in Semiconductors," Honours Thesis 1998, University of Western Australia. In another embodiment, transient photoconductive decay measurement subsystem 101 is similar to that used in Pratt et at "Minority carrier lifetime in n-type Bridgman grown $Hg_{1-x}Cd_xTe$" Journal of applied physics 54, no. 9 (1983): 5152-5157, and herein incorporated by reference in its entirety. A further example is given in T. Tomlin, "Spatial Mapping of Minority carrier lifetime in Mercury Cadmium Telluride," Honours Thesis 1995, University of Western Australia. In one embodiment, as shown in FIG. 3, an obtained voltage decay curve 300 denoted as $V_{me}(t)$ comprises a plurality of measurements comprising measurements 305, 306 and 307 of the voltage across the sample at corresponding times 301, 303, and 304. The time instant corresponding to each measurement within the plurality is separated from the time instant corresponding to the preceding measurement by a time interval $\Delta t$ (302), such as shown in FIG. 3.

Statistical analysis subsystem 204 performs statistical analyses which will be described later. In one embodiment, the statistical analysis subsystem 204 is implemented in hardware. In one embodiment, the statistical analysis subsystem 204 is implemented in software. In yet another embodiment, statistical analysis subsystem 204 is implemented in a combination of hardware and software. Different programming languages and systems can be used to implement statistical analysis subsystem 204, including, for example, SPSS, S, R, STATA, MATLAB™, SAS®, MICROSOFT™ EXCEL™, SQL and C++.

Data analysis subsystem 203 performs various functions, including preparing data for statistical analysis subsystem 204, collating the results of analysis performed by statistical analysis subsystem 204, performing further analysis of the results from statistical analysis subsystem 204 and presenting the results of these analyses. In one embodiment, the data analysis subsystem 203 is implemented in hardware. In one embodiment, the data analysis subsystem 203 is implemented in software. In yet another embodiment, data analysis subsystem 203 is implemented in a combination of hardware and software. Different programming languages and systems can be used to implement data analysis subsystem 203, including, for example, SPSS, S, R, STATA, MATLAB™, SAS™, MICROSOFT™ EXCEL™, SQL and C++.

Database 205 is used to store voltage decay curve data obtained from transient photoconductive decay subsystem 201, and data for intermediate processing performed by statistical analysis subsystem 204 and data analysis subsystem 203. Different programming languages and systems can be used to implement database 205, including, for example, SQL and MICROSOFT™ ACCESS™.

Interconnection 202 is used to connect the different subsystems together. These could include, for example, local area networks (LAN), campus area network (CAN), wide area networks (WAN). Interconnection 202 could encompass one or more subnetworks. Interconnection 202 could be implemented using various media including wireless, wired, optical network, and could encompass various technologies including Ethernet and IP-based networks.

In one embodiment, the system illustrated in FIG. 2 is used to compare one or more semiconductor samples. Then, for each of the one or more semiconductor samples, one or more voltage decay curves such as voltage decay curve 300 in FIG. 3, is measured using, for example, transient photoconductive decay measurement subsystem 201.

Figure 4:
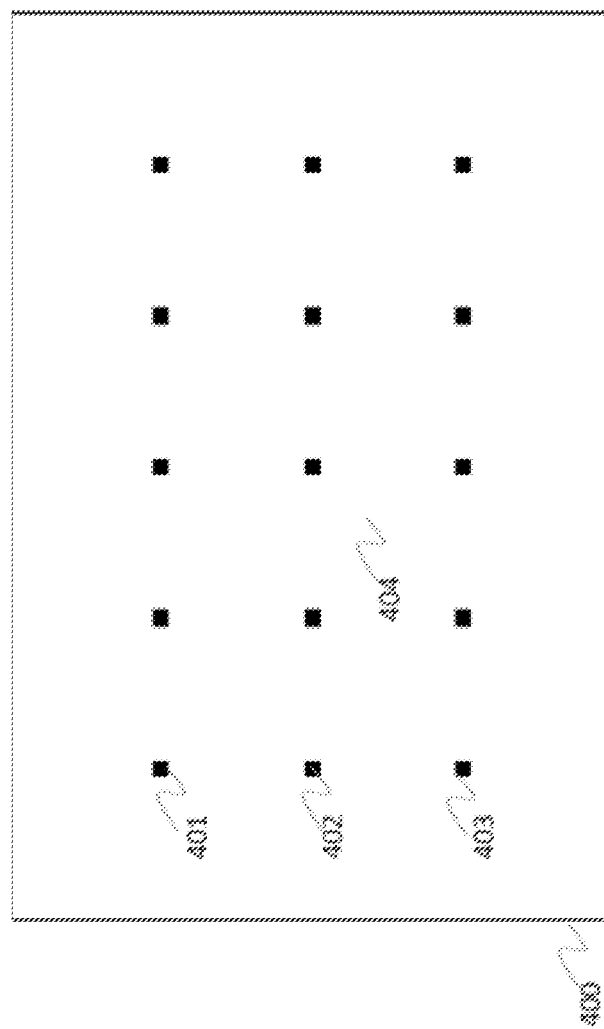
FIG. 4 shows a grid of points for mapping spatial non-uniformities across a semiconductor sample.

In another embodiment, the system illustrated in FIG. 2 is used to map spatial non-uniformities across a single semiconductor sample. In this embodiment, using transient photoconductive decay measurement subsystem 201, light is shone at different points across a semiconductor sample, and for each point a voltage decay curve is obtained. For example, in one embodiment, light is shone at each point, for example points 401, 402 and 403 within a grid of points 404 such as shown in FIG. 4 for sample 400 is created. Voltage decay curves such as voltage decay curve 300 of FIG. 3 as shown above are then obtained for each point.

As explained previously, the generation, movement and recombination of minority carriers which occurs within a semiconductor sample each time light is incident on a spot on the semiconductor sample using the transient photoconductive decay measurement subsystem 201 are random sub-processes which are part of a single overall random or stochastic process. Consequently, each obtained voltage decay curve represents the evolution of the population of minority carriers with time for one realization of this overall random process.

In one embodiment, in order to remove the impact of noise, light is shone on the same spot on the semiconductor sample a plurality of times. Then, each time light is shone on the spot, a corresponding voltage decay curve is obtained.

Figure 5A:
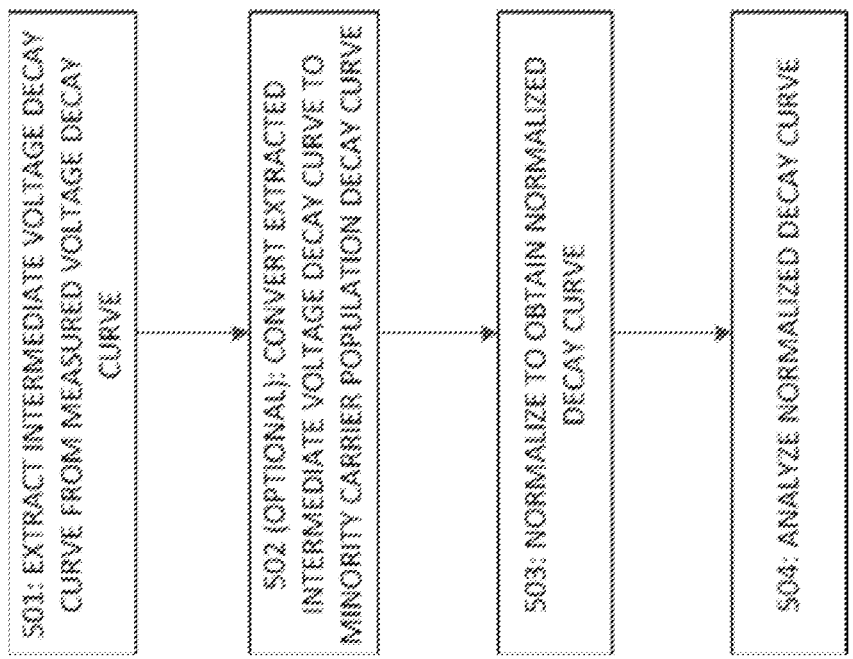
FIG. 5A shows one embodiment of an analysis performed on a voltage decay curve.

In one embodiment, the following analysis is applied to each obtained voltage decay curve as shown in FIG. 5A.

Figure 5B:
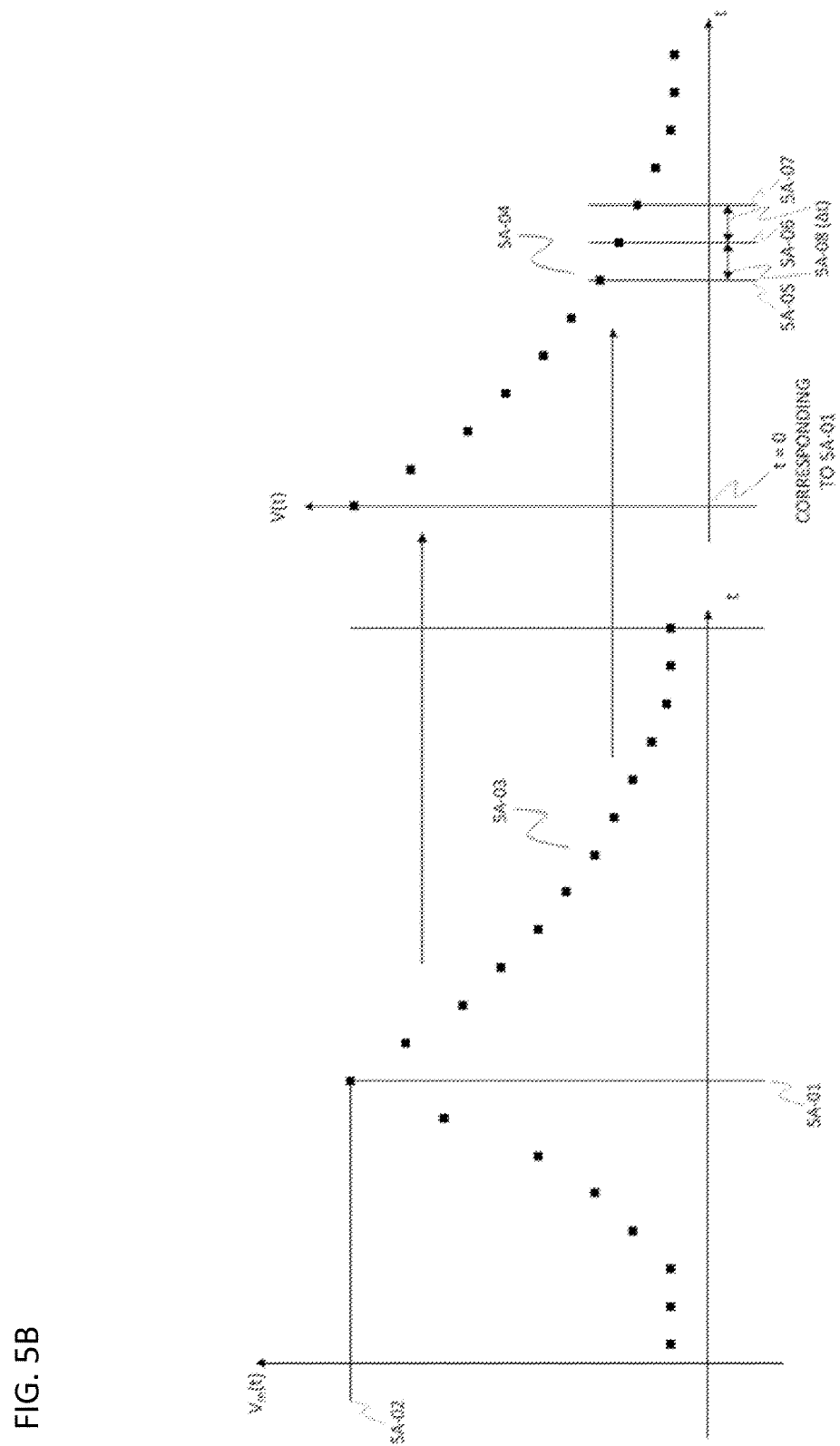
FIG. 5B shows an example of extracting readings to form an intermediate voltage decay curve V(t).

In step 501, using for example, data analysis subsystem 203, the segment of the measured voltage decay curve with times greater than the time corresponding to the peak of the voltage decay curve is extracted to form an intermediate voltage decay curve V(t). An example is shown in FIG. 5B. The time 5A-01 corresponds to the peak (5A-02) of the obtained voltage decay curve 5A-00. Then, the segment 5A-03 of the voltage decay curve 5A-00 for all times greater than time 5A-01 is extracted, to form intermediate voltage decay curve 5A-04. Each time instant on intermediate voltage decay curve 5A-04 is separated from the next time measurement by $\Delta t$ (5A-08), such as, for example, time instants 5A-05, 5A-06 and 5A-07. The intermediate voltage decay curve 5A-04 can be represented as V(n$\Delta t$), n=0, 1, 2 . . . N where n$\Delta t$ are the time instants.

In the embodiment where light is shone on the same spot a plurality of times and a corresponding measured voltage decay curve is obtained for each time, a plurality of corresponding intermediate voltage decay curves $V_k(n\Delta t)$ are obtained, k=1, 2, 3 . . . K. The corresponding intermediate voltage decay curves are then averaged out to provide a smoothed intermediate voltage decay curve $V_s(n\Delta t)$, that is:

$$V_S(n\Delta t) = \frac{\sum_{k=1}^{K} V_k(n\Delta t)}{K}$$

This is performed for n=0, 1, 2 . . . N.

In optional step 502, using for example, data analysis subsystem 203, the intermediate voltage decay curve V(n∆t) or smoothed intermediate voltage decay curve $V_s(n\Delta t)$ obtained in step 501 is converted to a minority carrier population decay curve p(t). Various approaches to perform this conversion are known to those of skill in the art and will not be explained further within this specification.

In step 503, in one embodiment, using for example, data analysis subsystem 203 the intermediate voltage decay curve V(n∆t) or smoothed intermediate voltage decay curve $V_s(n\Delta t)$ obtained in step 501 is normalized to the voltage at time t=0 to obtain a normalized decay curve $V_{no}(n\Delta t)$. In an alternate embodiment, if optional step 502 is performed, the p(t) obtained in step 502 is normalized to the minority carrier population at time t=0 to obtain a normalized decay curve $p_{no}(t)$.

The normalized decay curve represents a discrete estimate $S_e(n\Delta t)$, n=0, 1, 2 . . . N of the continuous time survival function S(t)=P[τ>t]. S(t) is the probability that minority carriers will survive, that is not recombine, until beyond time t. If, in step 501, a smoothed intermediate voltage decay curve is provided as an output, then the obtained normalized smoothed decay curve is a better discrete estimate $S_e(t)$ of S(t).

Figure 6:
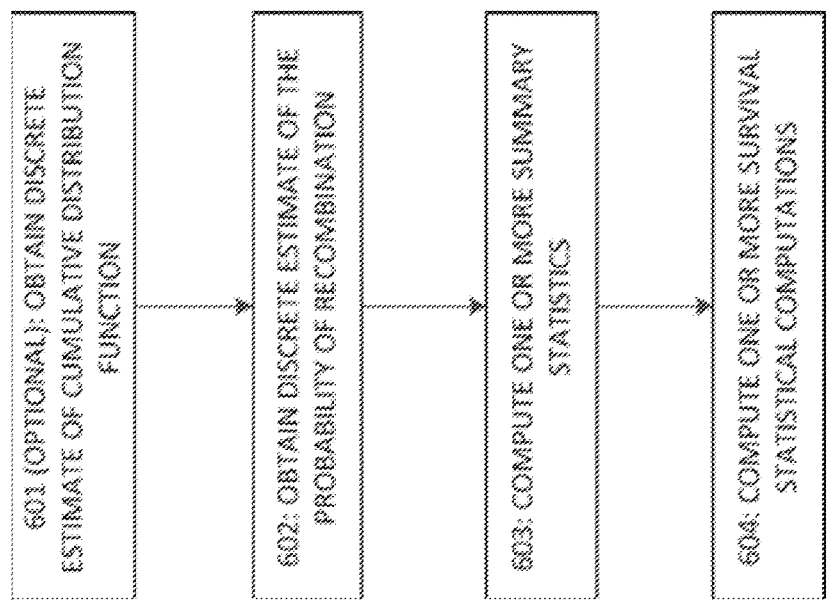
FIG. 6 shows one embodiment of step 504.

In step 504, $S_e(t)$ is analysed using, for example, statistical analysis subsystem 204. One embodiment of step 504 is shown in FIG. 6. The cumulative distribution function CDF(t)=P[τ≤t] is obtained by P[τ≤t]=1−S(t). In an optional embodiment, in step 601, a discrete estimate $CDF_e(n\Delta t)$ of the cumulative distribution function CDF(t) is obtained by computing 1−$S_e(n\Delta t)$, n=0, 1, 2 . . . .

In step 602, in one embodiment, an estimate of the probability of recombination between time [n∆t] and [(n+1)∆t], n=0, 1, 2 . . . is obtained. The probability is given by the probability mass function $PMF_e[(n+1)\Delta t]$, which is obtained by taking successive differences of the estimate of the survival function $S_e(t)$. That is, the estimate $PMF_e[(n+1)\Delta t]$, n=0, 1, 2 . . . is given by $S_e[n\Delta t]-S_e[(n+1)\Delta t]$. Alternatively, if in step 603, $CDF_e(n\Delta t)$ is calculated, then $PMF_e[(n+1)\Delta t]$ is given by $CDF_e[(n+1)\Delta t]-CDF_e[n\Delta t]$.

In step 603, one or more summary statistics are computed. In one embodiment, an estimate of the mean of τ denoted as E[τ] or $\mu_\tau$ is calculated. In one embodiment, $S_e(t)$ is used directly to calculate E[τ] performing the summation of $S_e(t)$ from n=1 onwards. In another embodiment $PMF_e[(n+1)\Delta t]$ is used.

In another embodiment, the variance of τ denoted as Var(τ) or alternatively $\sigma_\tau^2$ is computed.

Other summary statistical computations can be performed including moment generation, Laplace transform and characteristic function generation. Moments can also be calculated. Other expectations can also be calculated using the generalized formulae such as, for example $E(1/\tau^3)$ and $E(1/\tau^2)$.

In another embodiment, in step 604, one or more survival statistical computations are applied. In one embodiment, the discrete time hazard probability $\lambda_e[(n+1)\Delta t]$, which is the probability of recombination for a minority carrier between times [n∆t] and [(n+1)∆t] given that the minority carrier has not recombined before time [n∆t] is calculated. Mathematically this is given by:

$$\lambda_e[(n+1)\Delta t] = \frac{PMF_e[(n+1)\Delta t]}{S_e(n\Delta t)}$$

Alternatively it can be calculated as:

$$\lambda_e[(n+1)\Delta t] = 1 - \frac{S_e[(n+1)\Delta t]}{S_e(n\Delta t)}$$

Quantiles of $S_e(n\Delta t)$ can be calculated as well. For example, the lowest decile of $S_e(n\Delta t)$, that is, the time after which 90% of the minority carrier population at t=0 have not recombined can be calculated by determining when $S_e(n\Delta t)$ drops below 0.90. Similarly the highest quartile of $S_e(n\Delta t)$, that is, the time after which 25% of the minority carrier population at t=0 have not recombined can be calculated by determining when $S_e(n\Delta t)$ drops below 0.25.

Another survival statistical computation which can be performed is calculating the mean residual time E(τ−n∆t|τ≥n∆t). This gives the expected time until recombination for a minority carrier, given that the minority carrier survived up to time n∆t. This can be calculated using well known mathematical formulas and will not be discussed in detail within this specification.

Figure 7:
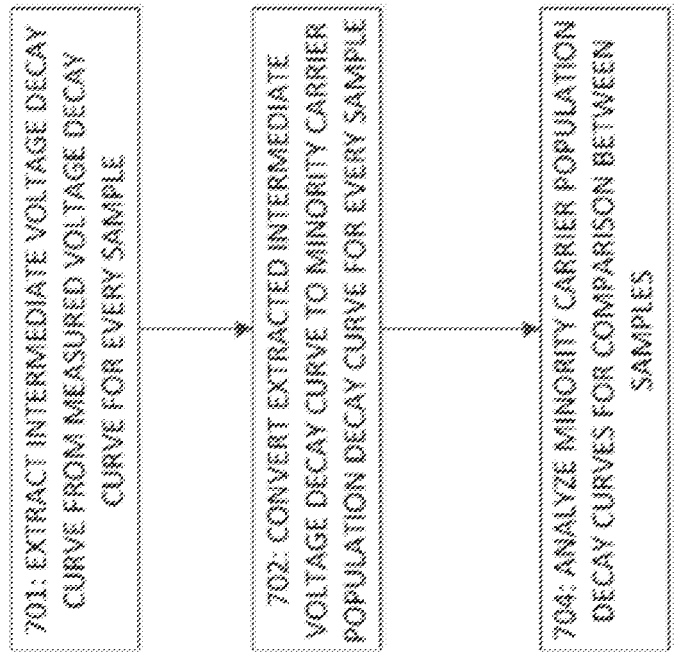
FIG. 7 shows an embodiment of a process to perform comparison between two or more samples, or two or more locations within the same sample.

It may be necessary to compare minority carrier decay behavior for two or more samples, or at two or more locations within the same sample, to determine if there is nonuniformity between samples or whether there is spatial nonuniformity within the same sample. Then, known mathematical techniques to compare survival behaviour for different populations of generated minority carriers can be employed. This involves using a process similar to that outlined in FIG. 5A, except that step 503 is not performed. An embodiment is shown in FIG. 7. Steps 701 and 702 are identical to steps 501 and 502, except that step 502 is not optional. These two steps are performed for every sample, or for every point or location within the same sample. These steps are implemented using, for example, data analysis subsystem 203 as previously detailed.

In step 704, the minority carrier population decay curves obtained in step 702 are analyzed to perform comparisons between samples. In one embodiment, in step 704, methods of semiparametric testing are used to detect spatial nonuniformities in the semiconductor sample or differences between semiconductor samples. In one embodiment, as described in, for example, p. 251-291 of N. Balakrishnan, and C. R. Rao "Handbook of statistics: advances in survival analysis. Vol. 23" Access Online via Elsevier, 2004, the Cox proportional hazard analysis model is used. This assumes that the discrete time hazard probabilities $\lambda_e[(n+1)\Delta t]$ for the samples are proportional to each other. In a further embodiment, results can be tested for validity of the proportional hazard assumption. Examples of tests for validity are described in D. Schoenfeld, "Partial residuals for the proportional hazards regression model." Biometrika vol. 69 no 0.1 pp. 239-241 (1982); and T. M. Thernau et al "Modeling Survival Data: Extending the Cox Model" New York: Springer-Verlag 2000.

In another embodiment, in step 704, various nonparametric comparison techniques can be used to analyse the p(t) obtained in step 702. In one embodiment, the Mantel-Cox or logrank test is used, as described in Section 7.3 and 7.7 of Klein et at "Survival Analysis: Techniques for Censored and Truncated Data" Springer, 1997. In another embodiment, the Gehan-Breslow test is used as described in the references E. A. Gehan, "A generalized Wilcoxon test for comparing arbitrarily singly-censored samples." Biometrika vol 52, no. 1-2 pp. 203-223 (1965); and N. Breslow "A generalized Kruskal-Wallis test for comparing K samples subject to unequal patterns of censorship." Biometrika vol. 57 no. 3 pp. 579-594 (1970). In another embodiment, the Tarone-Ware test is used as described in the reference R. E. Tarone et at "On distribution-free tests for equality of survival distributions." Biometrika vol 64 no. 1 pp. 156-160 (1977). In yet another embodiment, the tests proposed in T. R. Fleming et al "Counting processes and survival analysis" Wiley.com, 1991 are used. In another embodiment, one or more such comparisons are performed, depending on, for example, whether the survival curves to be compared cross with each other or the requirements of the analysis. In one embodiment, these tests are performed by statistical analysis subsystem 204. In another embodiment, these tests are performed by a combination of statistical analysis subsystem 204 and data analysis subsystem 203.

In yet another embodiment, in step 704, a combination of the previously described Cox proportional hazards analysis approach and the nonparametric approaches described above are used. Firstly, a visual check is performed to see if the discrete time hazard probabilities for the samples cross. If not, then the validity of the assumption of proportional hazards is tested. If the assumption of proportional hazards is valid, then the logrank test is used. If the discrete time hazard probabilities cross, a different test is used, such as the test outlined in A. Renyi "On the Theory of Order Statistics" Acta Mathematica Hungarica vol. 4 pp. 191-231, 1953.

Figure 8:
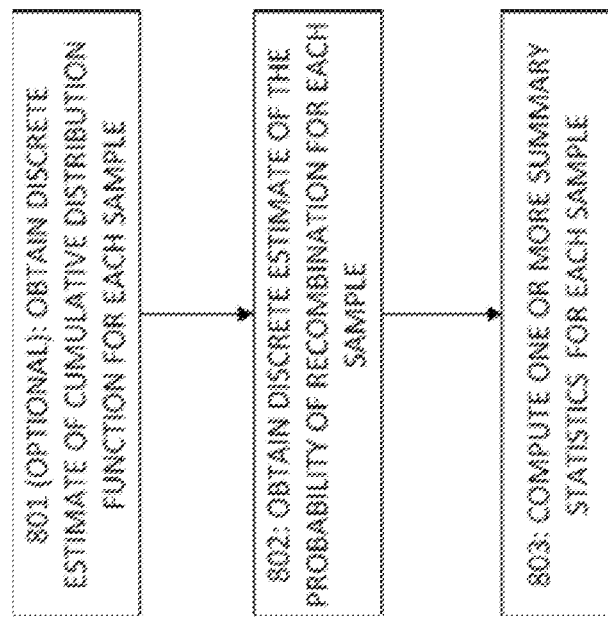
FIG. 8 shows an example flowchart to calculate and compare summary statistics.

In a further embodiment, in step 704, one or more combinations of analyses are performed. For example, once the non-parametric tests have been performed and differences between the populations have been observed, then the summary statistics for each sample or each point can be calculated and compared. An example flowchart is shown in FIG. 8. Steps 801-803 are similar to steps 601-603 respectively, and performed for each sample or each point within a sample using, for example, statistical analysis subsystem 204 as previously detailed.

The advantage of the new analysis approaches over the previous parametric analysis approaches is that there are no assumptions of the form of the minority carrier population decay curve p(t). This therefore overcomes the problems due to relying on the use of models with unrealistic assumptions. By using minority carrier population decay curves p(t) or converting to a normalized decay curve and applying the understanding that this can be converted to a discrete time estimate of the CDF, methods of probabilistic analysis can be applied as described above without having to perform fitting to models which are inherently unrealistic.

In an additional embodiment, one or more "windows" of interest are determined. Each of these windows comprises a lower bound and an upper bound, and the decay curve between these bounds is extracted. Then one or more statistical computations are performed using these one or more windows. For example, in one embodiment the mean of the values within the window given by $E[\tau|n_1 \Delta t \leq \tau \leq n_2 \Delta t]$; $n_1 = 0, 1, 2 \ldots$ is computed using known formulas. Similarly other computations such as calculation of variance, Laplace transform, characteristic function, moments can also be performed. In another embodiment, the survival statistical computations and the comparison of survival behavior techniques outlined above and in FIG. 7 are performed using these one or more windows.

Various methods can be used to determine the window size. In one embodiment, in order to analyse the decay of the minority carrier population within a localized region of interest surrounding the point where minority carriers are generated by the incidence of light, a window with lower bound $t=0$ and upper bound $t=t_{win}$ is set. The upper bound can be set in a variety of ways.

Figure 9:
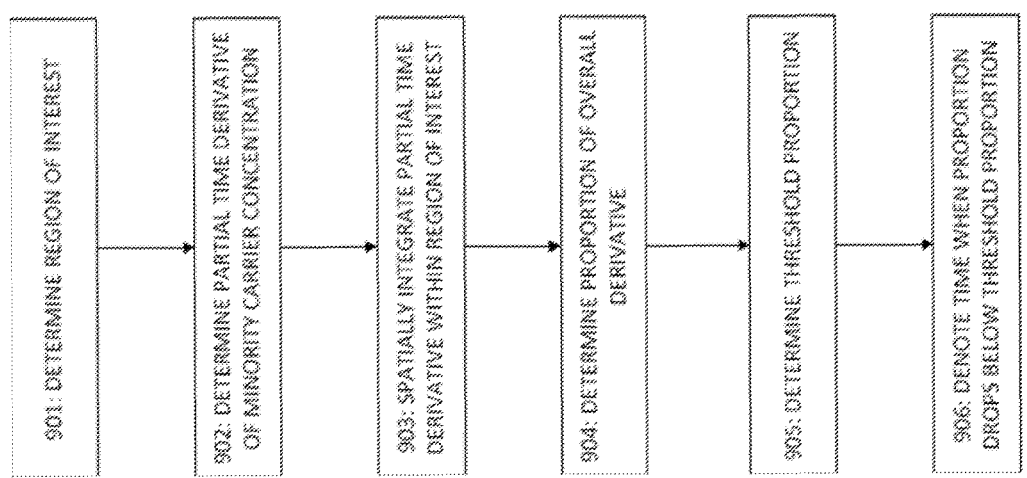
FIG. 9 shows a process to estimate an upper bound $t_{win}$ to calculate the proportion of recombination events taking place within a localized region of interest compared to the number of recombination events taking place within the entire semiconductor sample.

In one embodiment, $t_{win}$ is estimated by calculating the proportion of recombination events taking place within the localized region of interest compared to the number of recombination events taking place within the entire semiconductor sample, using one of the previously derived models such as in equations (1) and (2). An example is presented in FIG. 9.

Step 901: Determining the region of interest R

Step 902: Using the model, determining the partial time derivative of the minority carrier concentration $$\frac{\partial}{\partial t}[p(x, y, z, t)]$$

Step 903: Spatially integrating $$\frac{\partial}{\partial t}[(p(x, y, z, t)]$$

within the region of interest R using, for example, a triple integral $$\int\int\int_R \frac{\partial}{\partial t}[p(x, y, z, t)]$$

Step 904: Determining the proportion κ that the $\iiint_R \partial t/\partial[p(x, y, z, t)]$ comprises of the overall $$\frac{d}{dt}[p(t)],$$

that is $$\kappa = \frac{\int\int\int_R \frac{\partial}{\partial t}[p(x, y, z, t)]}{\frac{d}{dt}[p(t)]}$$

Step 905: Determining a threshold proportion $\kappa_T$

Step 906: Denoting the time when κ drops below $\kappa_\tau$ as $t_{win}$.

In another embodiment, $t_{win}$ is estimated by using one of the previously derived models to estimate the proportion of minority carriers within the localized area as compared to the entire semiconductor sample. An example is presented in FIG. 10:

Step 1001: Determining the region of interest R
Step 1002: Spatially integrating p(x, y, z, t) within region of interest R using the triple integral $\iiint_R$ p (x, y, z, t)
Step 1003: Determining the proportion κ that the $\iiint_R$ p (x, y, z, t) comprises of the overall p(t), that is $$\kappa = \frac{\iiint_R p(x, y, z, t)}{p(t)}$$

Step 1004: Determining a threshold $\kappa_T$ for the proportion
Step 1005: Denoting the time when κ drops below $\kappa_T$ as $t_{win}$.

Figure 10:
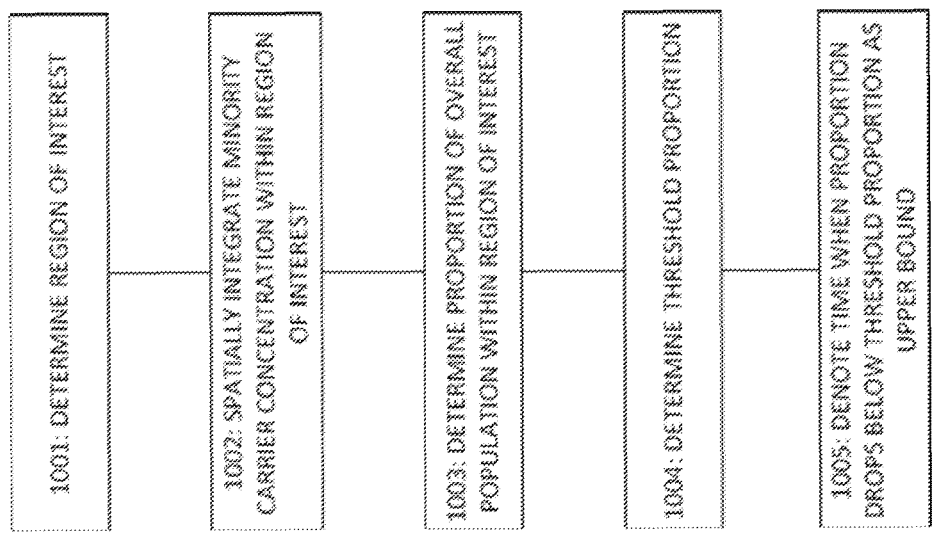
FIG. 10 shows a process to estimate an upper bound $t_{win}$ to calculate the proportion of minority carriers within the localized area as compared to the entire semiconductor sample.

An example of the approach in FIG. 10 is provided in Chapter 7 of Ramesh Rajaduray, "Investigation of Spatial Characterisation Techniques in Semiconductors," Honours Thesis 1998, University of Western Australia, for the model described in W. Van Roosbroeck, "Injected Current Carrier Transport in a Semi-Infinite Semiconductor and the Determination of Lifetimes and Surface Recombination Velocities." Journal of Applied Physics 26.4 (1955): 380-391 as explained earlier.

In another embodiment, $t_{win}$ is determined using, for example, numerical simulations such as Monte Carlo simulations.

In another embodiment, $t_{win}$ is determined using, for example, historical results from previous experiments or other types of characterization techniques.

In an embodiment, the setting of twin is performed using data analysis subsystem 203. In another embodiment, the setting of twin is performed using a combination of data analysis subsystem 203 and statistical analysis subsystem 204.

In another embodiment, once $t_{win}$ is known, then referring to FIG. 3 the number of measurements (M) needed to perform a valid analysis is determined. Referring to FIG. 3, for example if a minimum of $M_{min}$ samples are needed, then Δt (302) is set such that $$\Delta t \leq \frac{t_{win}}{M_{min}}$$

In a further embodiment, clustering is performed. For example, in the case where tests are performed to spatially characterize a semiconductor sample, different data points are grouped into spatial clusters based on different clustering metrics. In one embodiment, the clustering metric is the probability that two samples are drawn from the same population, based on their survival curves. For example, referring to FIG. 4, if the probability that the survival curves belonging to points 401 and 402 are drawn from the same population is above a threshold, then it is likely that points 401 and 402 have very similar parameters, that is, there is no spatial variation between these points. Then 401 and 402 belong to the same cluster. However if the probability that the survival curves belonging to points 401 and 403 are drawn from the same population is below a threshold, then it is likely that there is spatial variation between points 401 and 403. Then points 401 and 403 do not belong in the same cluster.

Continuing the above example, assume that 402 and 403 also belong in the same cluster. Then two clusters for the points A, B and C can be created:
Cluster 1: (401, 402)
Cluster 2: (402, 403)

This is an example of overlapping clusters, that is, where a point belongs to a plurality of clusters. In the example above, point 402 belongs to clusters 1 and 2. It is also possible to stipulate that clusters are non-overlapping, that is, where a point belongs to only one cluster. Then a given point will be assigned to the cluster which is the closest match.

In one embodiment, the clustering is performed using pairwise comparison, as demonstrated above. In another embodiment, the clustering is performed on the basis of summary statistics. In another embodiment, clusters are pre-defined using the results of other tests.

In a further embodiment, the clustering demonstrated above is extended to a plurality of semiconductor samples.

The methods explained above are not just limited to the transient photoconductive decay technique. The methods can be extended to other fields where a population is introduced and outputs related to the decay curves of the introduced population are readily available for measurement, so as to enable conversion into survival functions.

Although the algorithms described above including those with reference to the foregoing flow charts have been described separately, it should be understood that any two or more of the algorithms disclosed herein can be combined in any combination. Any of the methods, algorithms, implementations, or procedures described herein can include machine-readable instructions for execution by: (a) a processor, (b) a controller, and/or (c) any other suitable processing device. Any algorithm, software, or method disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire algorithm and/or parts thereof could alternatively be executed by a device other than a controller and/or embodied in firmware or dedicated hardware in a well known manner (e.g., it may be implemented by an application specific integrated circuit (ASIC), a programmable logic device (PLD), a field programmable logic device (FPLD), discrete logic, etc.). Also, some or all of the machine-readable instructions represented in any flowchart depicted herein can be implemented manually as opposed to automatically by a controller, processor, or similar computing device or machine. Further, although specific algorithms are described with reference to flowcharts depicted herein, persons of ordinary skill in the art will readily appreciate that many other methods of implementing the example machine readable instructions may alternatively be used. For example, the order of execution of the blocks may be changed, and/or some of the blocks described may be changed, eliminated, or combined.

It should be noted that the algorithms illustrated and discussed herein as having various modules which perform particular functions and interact with one another. It should be understood that these modules are merely segregated based on their function for the sake of description and represent computer hardware and/or executable software code which is stored on a computer-readable medium for execution on appropriate computing hardware. The various functions of the different modules and units can be combined or segregated as hardware and/or software stored on a non-transitory computer-readable medium as above as modules in any manner, and can be used separately or in combination.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

What is claimed is:

1. A method for improving accuracy of characterizing a semiconductor sample using transient photoconductive decay measurements, said method implemented using an analysis system comprising:
  a transient photoconductive decay measurement subsystem,
  a database,
  a data analysis subsystem, and
  a statistical analysis subsystem,
    said transient photoconductive decay measurement subsystem, database, data analysis subsystem and statistical analysis subsystem connected to each other by an interconnection,
  said method comprising the steps of:
  exciting the semiconductor sample by
    passing, using the transient photoconductive decay measurement subsystem, a current through the semiconductor sample,
      said passing causing a voltage across said sample, and
    shining light on one or more points in the semiconductor sample, said shining of light generating electron hole pairs at the one or more points in the semiconductor sample, and
      said generating electron hole pairs causing a change in a conductivity of said semiconductor sample;
  measuring, using the transient photoconductive decay measurement subsystem, one or more voltage decay curves based on the corresponding change in the conductivity at said one or more points in said semiconductor sample;
  extracting, using the data analysis subsystem, one or more intermediate voltage decay curves corresponding to the one or more measured voltage decay curves;
  obtaining, using the data analysis subsystem, one or more normalized decay curves corresponding to the one or more intermediate voltage decay curves, each of the said one or more normalized decay curves corresponding to one or more discrete estimates of survival functions;
  analyzing, using the statistical analysis subsystem, said obtained one or more normalized decay curves, said analyzing comprising obtaining one or more discrete estimates of probability of recombination corresponding to the one or more normalized decay curves, and computing one or more summary statistics corresponding to each of said obtained one or more discrete estimates of the probability of recombination; and
  determining, by either the statistical analysis subsystem or the data analysis subsystem, presence of nonuniformities within said semiconductor sample based on results of said analyzing, said nonuniformities comprising spatial nonuniformities; and
  mapping said spatial nonuniformities across the semiconductor sample.

2. The method of claim 1, wherein said computing one or more summary statistics comprises computing at least one of
  a mean;
  a variance;
  a moment generation function;
  a Laplace transform; and
  a characteristic function.

3. The method of claim 1, further comprising performing one or more survival statistical computations.

4. The method of claim 1, wherein said computing one or more summary statistics comprises computing a window.

5. The method of claim 4, wherein said computing said window comprises determining of an upper bound, further wherein said determining of said upper bound is based on at least one of
  estimating a proportion of recombination events taking place within a localized region of interest compared to a number of recombination events taking place within the entire semiconductor sample;
  estimating a proportion of minority carriers within the localized region of interest compared to a population of minority carriers within the entire sample;
  performing numerical simulations;
  historical results; and
  one or more results from one or more other characterization techniques.

6. A method for improving accuracy of characterizing a semiconductor sample using transient photoconductive decay measurements, said method comprising:
  exciting the semiconductor sample by
    passing a current through the semiconductor sample,
      said passing causing a voltage across said sample, and
    shining light on a plurality of points in the semiconductor sample, wherein for each of said plurality of points, said shining of light generating electron hole pairs, and
      said generating electron hole pairs causing a change in the voltage across said sample;
  measuring a plurality of voltage decay curves, each of said plurality of voltage decay curves corresponding to each of said plurality of points in said semiconductor sample, and
    each of said plurality of voltage decay curves based on the change in the voltage across said sample;
  extracting a plurality of intermediate voltage decay curves corresponding to said plurality of measured voltage decay curves;
  converting said extracted plurality of intermediate voltage decay curves to a plurality of minority carrier population decay curves;
  performing one or more comparisons of survival behavior using said plurality of minority carrier population decay curves; and
  determining presence of nonuniformities within said semiconductor sample based on said performing one or more comparisons of survival behavior, said nonuniformities comprising spatial nonuniformities; and
  mapping the spatial nonuniformities across the semiconductor sample.

7. The method of claim 6, wherein said performing one or more comparisons of survival behavior comprises using one or more methods of semiparametric testing.

8. The method of claim 6, wherein said performing one or more comparisons of survival behavior comprises using one or more nonparametric comparisons.

9. The method of claim 6, wherein said performing one or more comparisons of survival behavior comprises using a combination of analyses.

10. The method of claim 6, wherein said performing one or more comparisons of survival behavior comprises computing one or more summary statistics.

11. The method of claim 6, wherein said determining presence of nonuniformities comprises performing clustering.

12. A method for improving accuracy of comparing a plurality of semiconductor samples using transient photoconductive decay measurements, said method comprising:

exciting said plurality of semiconductor samples by
passing a current through each of said plurality of semiconductor samples, said passing causing a voltage across each of said plurality of semiconductor samples, and
shining light on one or more points in each of said plurality of semiconductor samples, wherein for each of said one or more points,
said shining of light generating electron hole pairs, and
said generating electron hole pairs causing a change in the voltage across said corresponding semiconductor sample;
measuring a plurality of voltage decay curves created based on said changes in voltage in said plurality of semiconductor samples;
extracting a plurality of intermediate voltage decay curves corresponding to said plurality of measured voltage decay curves;
converting said extracted plurality of intermediate voltage decay curves to a plurality of minority carrier population decay curves;
performing one or more comparisons of survival behavior using said plurality of minority carrier population decay curves; and
determining presence of nonuniformities within said plurality of semiconductor samples based on said performing one or more comparisons of survival behavior.

13. The method of claim 12, wherein said performing one or more comparisons of survival behavior comprises using one or more methods of semiparametric testing.

14. The method of claim 12, wherein said performing one or more comparisons of survival behavior comprises using one or more nonparametric comparisons.

15. The method of claim 12, wherein said performing one or more comparisons of survival behavior comprises using a combination of analyses.

16. The method of claim 12, wherein said performing one or more comparisons of survival behavior comprises computing one or more summary statistics.

17. The method of claim 12, further comprising performing mapping of spatial nonuniformities for each of said plurality of semiconductor samples.

18. The method of claim 12, wherein said performing one or more comparisons of survival behavior comprises computing a window.

* * * * *